(12) United States Patent  
Balazovskij et al.

(10) Patent No.: US 10,786,577 B2  
(45) Date of Patent: Sep. 29, 2020

(54) PHARMACEUTICAL COMPOSITION COMPRISING GLUTATIONE DISULFIDE AND GLUTATHIONE DISULFIDE S-OXIDE

(71) Applicant: OBSCHESTVO S OGRANICHENNOY OTVETSTVENNOSTJU "IVA FARM", St.Petersburg (RU)

(72) Inventors: Mark Borisovich Balazovskij, St. Petersburg (RU); Viktor Georgievich Antonov, St. Petersburg (RU); Oleg Aleksandrovich Ignatenko, St. Petersburg (RU)

(73) Assignee: OBSCHESTVO S ORGANICHENNOY OTVETSTVENNOSTJU "IVA FARM", St. Petersburg (RU)

( * ) Notice: Subject to any disclaimer, the term of this patent is extended or adjusted under 35 U.S.C. 154(b) by 0 days.

(21) Appl. No.: 16/603,042

(22) PCT Filed: Jul. 17, 2018

(86) PCT No.: PCT/RU2018/000471  
§ 371 (c)(1),  
(2) Date: Oct. 4, 2019

(87) PCT Pub. No.: WO2019/098877  
PCT Pub. Date: May 23, 2019

(65) Prior Publication Data  
US 2020/0121802 A1 Apr. 23, 2020

(30) Foreign Application Priority Data

Nov. 17, 2017 (RU) .................. 2017140106

(51) Int. Cl.
| | |
|---|---|
| A61K 47/64 | (2017.01) |
| A61P 31/14 | (2006.01) |
| A61P 31/04 | (2006.01) |
| A61K 33/243 | (2019.01) |
| A61K 31/155 | (2006.01) |
| A61K 31/4709 | (2006.01) |

(Continued)

(52) U.S. Cl.  
CPC ............ *A61K 47/64* (2017.08); *A61K 31/155* (2013.01); *A61K 31/4709* (2013.01); *A61K 33/243* (2019.01); *A61K 38/063* (2013.01); *A61K 38/212* (2013.01); *A61K 39/205* (2013.01); *A61P 31/04* (2018.01); *A61P 31/14* (2018.01)

(58) Field of Classification Search  
CPC .. A61K 47/64; A61K 39/205; A61K 31/4709; A61K 38/212; A61K 33/243; A61K 31/155; A61K 38/063; A61P 31/04; A61P 31/14

See application file for complete search history.

(56) References Cited

U.S. PATENT DOCUMENTS

| 6,013,632 A | 1/2000 | Jones | |
|---|---|---|---|
| 2002/0002136 A1 | 1/2002 | Hebert | |
| 2005/0054580 A1* | 3/2005 | Kozhemyakin | A61K 33/24 514/7.9 |

FOREIGN PATENT DOCUMENTS

| RU | 2144374 C1 | 1/2000 |
|---|---|---|
| RU | 2153351 C2 | 7/2000 |

OTHER PUBLICATIONS

Huang et al, Biochemical Pharmacology, 2002, 64, 1049-1056 (Year: 2002).*

(Continued)

*Primary Examiner* — Sudhakar Katakam  
(74) *Attorney, Agent, or Firm* — Muncy, Geissler, Olds & Lowe, PC

(57) ABSTRACT

Pharmaceutical composition comprising glutathione disulphide or pharmaceutically acceptable organic or inorganic salt thereof and glutathione disulfide S-oxide of the following structure:

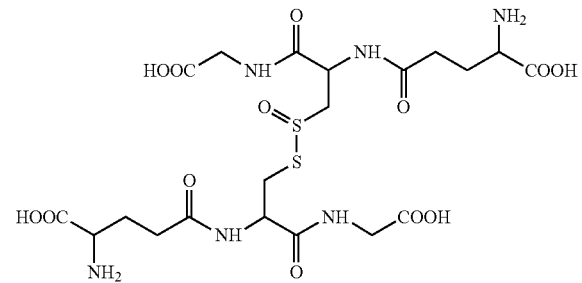

or pharmaceutically acceptable organic or inorganic salt thereof for eliminating dose-related toxicity and enhancing the therapeutic activity of a pharmacologically active compound in the treatment of infectious and non-infectious diseases is provided. Typically, the composition comprises glutathione disulfide S-oxide in an amount of 0.01-10% by weight of the total composition, and additionally a metal (Me) in the form of coordination compound(s) containing Me-S-glutathione bond, said metal is selected from the platinum group, typically it is platinum. The amount of d-metal coordination compound administered to a patient can be $10^{-3}$ to $10^{-15}$ mol/kg of body weight. The composition can be used in combination with pharmacologically active compound, which is an anticoagulant, factor Xa inhibitor, antimicrobial or antiviral agents to increase their therapeutic activity and eliminate dose-related toxicity.

14 Claims, 6 Drawing Sheets

(51) Int. Cl.
   *A61K 38/06*   (2006.01)
   *A61K 38/21*   (2006.01)
   *A61K 39/205*  (2006.01)

(56) References Cited

OTHER PUBLICATIONS

Xiong et al, Antioxidants & Redox Signaling, 2011, vol. 15, No. 1, 233-270 (Year: 2011).*
Ghezzi, Biochimica et Biophysica Acta, 2013, 1830, 3165-3172 (Year: 2013).*
Junfa LI et al.; "Glutathiolation of Proteins by Glutathione DisulfideS-Oxide Derived from S-Nitrosoglutathione: Modifications of Rat Brain Neurogranin/RC3 and Neuromodulin/Gap-43"; J. Biol. Chem., 2001, vol. 276, No. 5, pp. 3098-3105.

* cited by examiner

PHARMACEUTICAL COMPOSITION COMPRISING GLUTATIONE DISULFIDE AND GLUTATHIONE DISULFIDE S-OXIDE

CROSS REFERENCE TO RELATED APPLICATIONS

This nonprovisional application is a continuation of International Application No. PCT/RU2018/000471, which was filed on Jul. 17, 2018, and which claims priority to Russian Patent Application No. RU 2017140106, which was filed in Russia on Nov. 17, 2017, and which are both herein incorporated by reference.

FIELD OF THE INVENTION

The present invention relates to the pharmaceutical industry and to the medicine, namely to the field of preparation of medicaments, and can be used in pharmacology, medicine and veterinary medicine.

BACKGROUND OF THE INVENTION

Increasing the therapeutic efficacy of pharmacological molecules by optimizing their pharmacokinetics and/or pharmacodynamics, and/or reducing toxicity through chemical modification of the drug molecule and/or its concomitant use with another chemical compound or compounds is one of the directions for developing new generation drugs exhibiting their activity in physiologically more optimal doses.

At present, a substance is known—oxidized glutathione (glutathione oxidized, glutathione disulfide, GSSG), which is a dimer of glutathione tripeptide, γ-glutamylcysteinyl glycine, in which two molecules of said tripeptide are linked to each other via a covalent disulfide bond between cysteine residues. Both the tripeptide glutathione (glutathione reduced, GSH) and its dimer GSSG are natural metabolites and are present in tissues and biological fluids of humans and animals [Isabella Dalle-Donne et al. *S-glutathionylation in protein redox regulation/Free Radical Biology & Medicine*, 2007, V. 43, pp. 883-898; Калинина Е. В. и др. Роль глутатиона глутати онтранс феразы и глутар едоксина в регуляции редокс- зависимых процессов/Успехи биолог ической химии 2014, Т. 54, с. 299-348].

It is known in the art that oxidized glutathione (GSSG) itself has a variety of pharmacological activities. In particular, the ability of oxidized glutathione to enhance the production of a wide range of cytokines controlling a complex of protective reactions of the body, including antiviral, antibacterial, antitumor, antifibrotic action is shown.

Thus, Patent RU 2089179 C1, publ. 10 Sep. 1997] and Patent WO 9721444 A1, publ. 19 Jun. 1997) disclose use of oxidized glutathione and pharmaceutical compositions thereof for the treatment of oncological, infectious, immunological, neoplastic and hematological diseases, in which the stimulation of endogenous production of cytokines and hematopoietic factors is appropriate.

Patent RU 2206334 C1, publ. 20 Jun. 2003, Patent RU 2208452 C1, publ. 20 Jul. 2003), and Patent RU 2208453 C1, publ. 20 Jul. 2003 disclose use of pharmaceutical compositions comprising oxidized glutathione for increasing resistance (tolerance) of the body to the thermal effects of the environment, to increased pressure of the respiratory gas medium and to motion sickness, respectively.

The dosage form of oxidized glutathione is certified for use and exhibits an immunomodulating, hepatoprotective, hematopoietic effect, as well as pharmacological effects regulating redox processes in the body [http/www.rlsnet.ru/tn_index_id_10764.htm].

It is also known in the art developing of composites of oxidized glutathione or pharmaceutically acceptable salts thereof with platinum or palladium compounds (in particular composite consisting of disodium salt of oxidized glutathione with cis-diaminodichloroplatinum) providing regulation of endogenous production of cytokines and/or hematopoietic factors as well as processes of metabolism, proliferation, differentiation and apoptosis in normal and transformed cells and used for the treatment of cancer, infectious, immunological, hematological, ischemic, neurodystrophic, metabolic diseases [Patent RU 2144374 C1, publ. 20 Jan. 2000 Patent RU 2153350 C1, publ. 27 Jul. 2000; U.S. Pat. No. 6,312,734 B1, publ. 6 Nov. 2001].

In addition, combined agents comprising glutathione disulphide are known.

Thus, document [patent application WO 1998030228 A1, publ. 16 Jul. 1998] discloses use of oxidized glutathione (GSSG) alone or in combination with reduced form of glutathione (GSH), or in combination with ascorbate-2-phosphate, or in combination with N-acetyl-L-cysteine for the treatment of influenza viral infections.

Patent RU 2482868 C1, publ. 27 May 2013 describes a combination of glutathione disulfide (GSSG) in the form of disodium salt with lipoic acid in the form of sodium salt and coordination compounds formed by palladium, copper and reduced glutathione (GSH), which has hypoglycemic, hypocholesterolemic, hypolipidemic and/or antioxidant activity.

The closest analogue is a pharmaceutical composition, which is a drug disclosed in the Patent RU 2153351 C2, publ. 27 Jul. 2000, comprising oxidized glutathione GSSG and its pharmaceutically acceptable salts in combination with a prolongator, which composition regulates the endogenous production of cytokines and hematopoietic factors. Ascorbic acid, dimethylsulfoxide, inosine (hypoxanthine-9-D-ribofuranoside), cystamine (2,2'-dithiobis[ethylamine]), platinum compounds (for example, platinum chloride) are used as prolongators of the action of oxidized glutathione.

The disadvantage of said known drug as well as of all abovementioned agents is a limited use in medicine due to a number of factors. In particular, GSSG has a very short half-life in the range of 5-10 seconds after administration, which requires some training and appropriate qualification of healthcare personnel to determine the exact place of administration to obtain the desired therapeutic effect of the drug, or to increase the dose and multiplicity of administration. Said problem is partially solved by using a large number of prolonging compounds as described in RU 2153351, but this increases the potential danger of the agent for the patient and requires careful selection of combination of GSSG and a prolongator. Combined or sequential use of the combination of GSSG and a prolongator in complex therapy with other drugs additionally requires to take into account the similarity of pharmacokinetics to obtain the expected therapeutic effect in the absence of negative changes in the toxicity profile of the administered therapy. The developing of a combination of GSSG and any prolongator requires the use of additional processing equipment, the including an additional step or steps in the process of production of the drug substance and the corresponding dosage form, the expansion of the list of excipients. Despite the existing limitations in the use of the oxidized glutathione-based drug, GSSG is of undoubted interest for pharmacological solutions, which is associated with its biological activity, a feature of metabolism in pathological processes that adversely affect the therapeutic efficacy of drugs, which reduces the efficacy and safety of therapy.

DISCLOSURE OF THE INVENTION

The object of the present invention is to provide a novel pharmaceutical composition having high efficacy and potentiating activity toward pharmacologically active molecules from various pharmacotherapeutic groups. In particular, the objective is to optimize the pharmacodynamics and, ultimately, the pharmacodynamics of GSSG in order to make it possible to use smaller doses to obtain the necessary therapeutic effect when administered to a patient in need thereof, by inhalation, enterally, parenterally, with external application both alone and in combination with other pharmacologically active substances in a single dosage form. The pharmacologically active substance can be selected from any pharmacotherapeutic group, including antimicrobial and antiviral drugs, anticoagulants, factor Xa inhibitors; modulators of the activity of the cell membrane ion channels; other pharmaceuticals for which optimization of pharmacodynamics and/or pharmacokinetics, and/or reducing of toxicity will be achieved.

Both the pharmaceutical composition and the pharmaceutical combination can be used as a medicament comprising additional excipients.

The technical result of this invention is to reduce a single or a course dose and, therefore, to decrease the dose-related toxicity at the established therapeutic dose of the pharmacologically active substance; to enhance the efficacy of therapeutically active agents from various pharmacotherapeutic groups and, accordingly, to decrease their single or course dose and, therefore, to reduce dose-related toxicity.

Said technical result is achieved by providing a novel pharmaceutical composition, which is a drug comprising a combination of glutathione disulfide (GSSG) or pharmaceutically acceptable organic or inorganic salt thereof and glutathione disulfide S-oxide (GS(O)SG) or pharmaceutically acceptable organic or Inorganic salt thereof in therapeutically effective amounts, together with pharmaceutically acceptable excipients and pharmacologically active molecules from any pharmacotherapeutic group, for which the reducing in a single or a course dose has been established and, accordingly, the reducing in dose-related toxicity.

Typically, the pharmacologically active compound is selected from the following pharmacotherapeutic groups:
  anticoagulants, factor Xa inhibitors, in particular amidine hydrochloride;
  antimicrobial and antiviral drugs, in particular moxifloxacin, antigenic material of anti-rabies vaccine, interferon α;
  modulators of activity of the cell membrane calcium channel, in particular nifedipine; for which the optimization of pharmacodynamics and/or pharmacokinetics, and/or toxicity reduction will be achieved.

Usually, the amount of glutathione disulphide S-oxide is 0.01-10% by weight of the total composition.

Also, the composition may further comprise a d-metal (Me), preferably from platinum group, even more preferably platinum, presented in the form of the coordination compound(s) containing Me-S-glutathione bond.

The amount of d-metal added into the composition as the coordination compound does not exceed physiologically acceptable values for the given d-metal. However, this value may be exceeded in the case where large amounts of metal added in the form of coordination compound are required to achieve a therapeutic effect.

The amount of d-metal in the composition varies from $1\times10^{-10}$ mol to $1\times10^{-3}$ mol per 1 kg of the composition, preferably, $1\times10^{-5}$ mole per 1 kg of the composition.

Provided composition may be prepared for external, inhalational, enteral or parenteral administration.

Characteristics of Components

Glutathione disulphide (or oxidized glutathione, GSSG) is a dimer of tripeptide glutathione, γ-glutamylcysteinylglycine, wherein two molecules of said tripeptide are linked to each other via a covalent disulfide bond between the cysteine residues. According to the present invention, glutathione disulfide in the form of a salt with an alkali or alkaline earth metal can be prepared by any method known in the art [Patent RU 2144374 C1, publ. 20 Jan. 2000].

Glutation disulfide S-oxide (also called glutathione thiosulfinate or GS(O)SG), has the following structure:

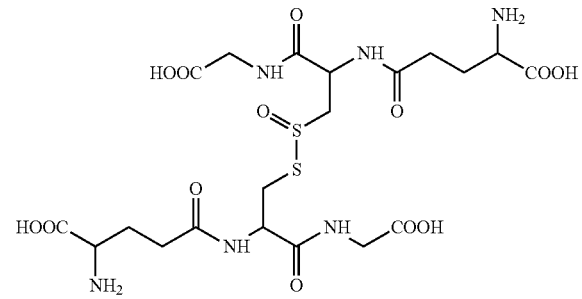 [SMILES: NC(CCC(=O)NC(CSS(=O)CC(NC(=O)CCC(N)C(=O)O)C(=O)NCC(=O)O)C(=O)NCC(=O)O)C(=O)O]

Glutation disulfide S-oxide is characterized by similar pharmacokinetics to oxidized glutathione, and thus, it is a negative regulator of enzymes of oxidized glutathione decomposition it, therefore, acts as a prolongator for GSSG, optimizing its pharmacokinetics, potentiating biological effects of oxidized glutathione, which optimizes the pharmacodynamics of GSSG and allows use of smaller doses of GSSG for obtaining the desired therapeutic effect. Transition to lower levels is one of the key conditions for reducing the toxicity of the active principle of a drug. Therefore, glutathione disulfide S-oxide optimizes pharmacokinetics, pharmacodynamics, increases safety of GSSG use, all of which is a condition for pharmacoeconomic criteria optimization for use combination of glutathione disulfide S-oxide and GSSG in therapeutic practice in comparison with GSSG.

Molecules of glutathione disulfide and glutathione disulfide S-oxide are able to form weak intermolecular interactions, such as van der Waals interactions, with the active principle of drugs, optimizing their therapeutic properties by influencing the pharmacokinetics and/or pharmacodynamics, and/or toxicity.

"Coordination compounds" refer to compounds containing a group of ions or neutral molecules called ligands, placed in a certain order (coordinated) around the central atom (ion) called complexing agent.

"d-metals", "transition metals" and "transition elements" are identical, and refer to the chemical elements of the periodic system, in which electrons fill the d-sublevels.

"Pharmaceutically acceptable excipients" are substances known to a person skilled in the art and suitable for obtaining of a medicament comprising the composition of the present invention for external, inhalational, enteral, parenteral or other way of administration. For example, any known pharmaceutically acceptable inorganic or organic carriers, preservatives, solubilizers, stabilizers, wetting agents, emulsifiers, sweeteners, colorants, flavorants, salts for regulating the osmotic pressure, buffers, masking agents or antioxidants and other necessary components can be used as excipients.

"Pharmaceutically acceptable" means compounds that do not cause toxic or other undesirable effects when administered to a patient.

A "therapeutically effective agent" means any substance which is used for therapeutic purposes.

A "patient" refers to man or other mammal, birds, amphibians or fish, the body of which one way or another is administered the composition or its combination with a known pharmacologically active compound, in particular, with the factor Xa-inhibitor amidine hydrochloride; antimicrobial agent moxifloxacin, antigenic material of antiviral anti-rabies vaccine, antiviral agent interferon α; calcium channel inhibitor nifedipine.

DISCLOSURE OF THE INVENTION

Figure 1:
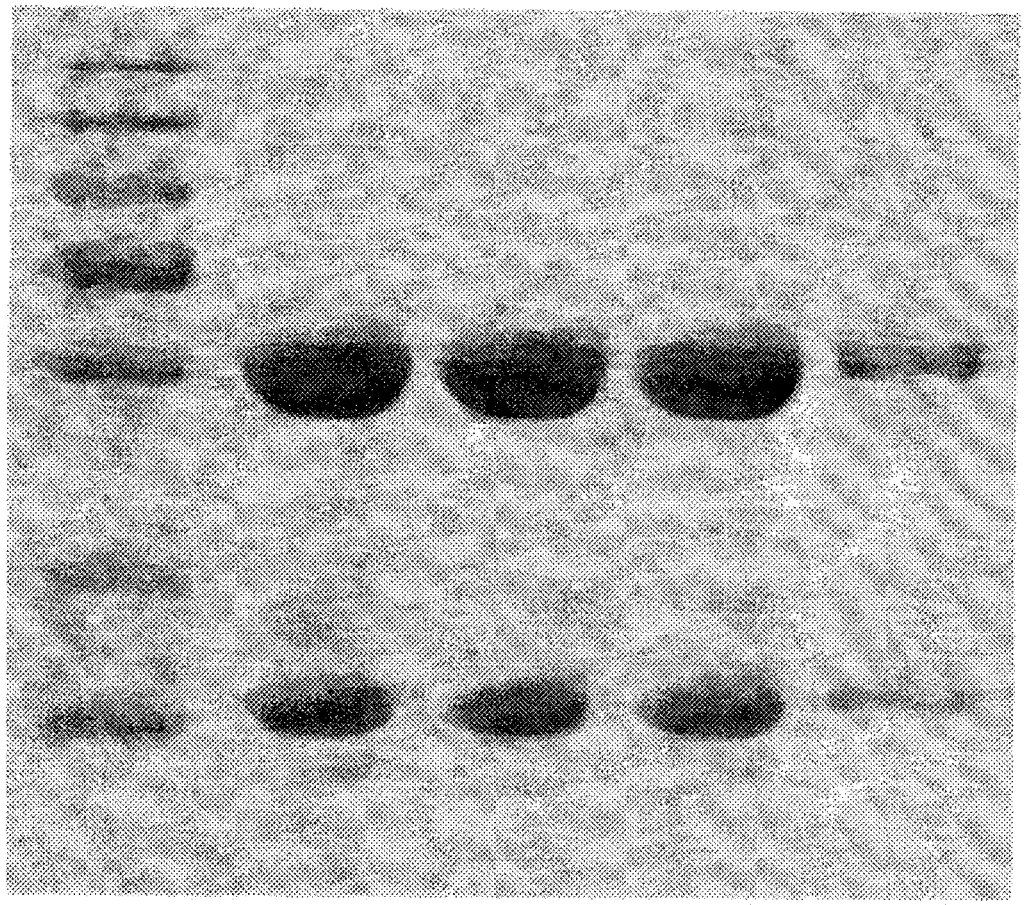
FIG. 1—Electrophoregram of the formulation of the monoclonal antibody dissolved in various solutions stored at a temperature of 37° C. Lane 1—size standards (Fermentas PageRuler™ Prestained Protein Ladder); lane 2—sample 2; lane 3—sample 3, lane 4—sample 4, lane 5—sample 1.

The present invention is illustrated by specific embodiments of the invention that are illustrative in nature and do not in any way limit the scope of the claims claimed.

Abbreviations:
GSH—glutathione (reduced glutathione),
GSSG—oxidized glutathione (glutathione disulfide),
$GSO_3H$—glutathionesulfonic acid,
GS(O)SG—glutathione disulfide S-oxide or sulfoxide;
$GS(O_2)SG$—glutathione disulfide S-dioxide;
HPLC—high-performance liquid chromatography;
PAAG—polyacrylamide gel;
SDS—sodium dodecyl sulfate.

Methods for Preparing Compositions

Method A

To solution of sodium salt of glutathione disulfide derived from L-glutathione (Example 2), glutathione disulfide S-oxide synthesized according to the procedure (Example 1) was added. The amount of glutathione disulfide S-oxide can be 0.1-10% by weight of the total composition. In practical embodiment, in particular Examples 3 and 4, the amount of glutathione disulphide S-oxide was 2% and 4%, respectively, based on the weight of the total composition. The provided method makes it possible to control the content of glutathione disulfide S-oxide with high accuracy.

Method 8

To the obtained solution of glutathione disulfide sodium salt in an aqueous solution of sodium hydroxide an excess of hydrogen peroxide was added at a reduced temperature, usually 0-5° C., to generate glutathione disulfide S-oxide in situ. In one embodiment (Example 5), 127 g of 6% hydrogen peroxide was added at a temperature of not higher than +3° C. The amount of glutathione disulfide S-oxide was 5% by weight of the total composition.

The composition obtained by method A or B is characterized by the ability to influence the formation and stability of the disulfide bond in proteins (Examples 5 and 12), and hence the folding of the protein, which allows to form and stabilize the native conformation of the protein, i.e. a conformation in which the protein possesses functional activity, in particular the conformation of a drug represented by a protein product, which is a monoclonal antibody consisting of two heavy and two light peptide chains linked via disulfide bonds into a functionally active molecule having therapeutic activity (Example 5).

The composition obtained by method A or B is characterized by the ability to increase the expression of the enzymes of the second phase of xenobiotic detoxification (Example 13), which makes it possible to use it alone as a toxicomodifying agent, i.e. an agent that reduces the toxic effect of various chemical molecules, including a complex of dose-dependent toxic side effects of administered pharmacotherapeutic agents.

The composition obtained by method A or B can be used in combination for the preparation of medicaments in conjunction with other known pharmacologically active and widely used therapeutically molecules: in particular, an anticoagulant, factor Xa inhibitor amidine hydrochloride (Example 8); antibiotic moxifloxacin; antiviral agents, antigenic material of anti-rabies vaccine and interferon α (Examples 9, 10, 14); calcium channel inhibitor nifedipine (Example 11), for which a dose reduction and, accordingly, a decrease in dose-related toxicity is established.

Example 1. Method for the Preparation of Glutathione Disulfide S-Oxide (GS(O)SG)

To a solution of 100 g of reduced L-glutathione substance (GSH) in 100 ml of water, 150 ml 30% solution of peracetic acid in acetic acid was added dropwise with stirring at a temperature of 0-5° C. for 30-40 minutes. After dropwise addition, the reaction mass was stirred at a temperature of no higher than 5° C. for 1 hour, after which it was frozen and lyophilized for 24 hours. 110 g of a substance was obtained as a white foam, which contains mixture of components according to HPLC analysis (40% $GSO_3H$, 55% GS(O)SG, 5% $GS(O_2)SG$).

The lyophilisate was dissolved in 400 ml of water and purified using the preparative HPLC (column YMC-Actus Triart Prep C18-S 50×250 mm, water as eluent), fractions containing the title compound with a purity above 95% were combined, evaporated to a volume of 700 ml, and lyophilized. 42 g of the desired compound glutathione disulphide S-oxide was obtained (as a mixture of diastereomers) with a purity of 95+% (HPLC).

Example 2. Preparation of Oxidized Glutathione (Glutathione Disulphide)

To a suspension of 2760 g of reduced L-glutathione in 7 L of water, 2245 g of 16% solution of sodium hydroxide was added with stirring at a temperature of no higher than 17° C. After complete dissolution of glutathione, a mixture was cooled and 2546 g of 6% hydrogen peroxide was added at a rate of 30-50 ml/min with stirring at a reaction mass temperature of not more than +15° C. After peroxide addition, the resulting solution was stirred at a predetermined temperature for an additional 1 hour. After completion of the reaction (HPLC control), a solution containing 2.95 kg of the disodium salt of glutathione disulphide in 11.5 L of water was obtained, which was cooled to 3° C. The chemical purity of the product, disodium salt of glutathione disulphide was more than 98.5% (HPLC control), which does not require additional procedures for product isolation.

Example 3. Preparation of the Composition (Drug) of Glutathione Disulfide with the Given Glutathione Disulfide S-Oxide Content To glutathione disulfide disodium salt prepared in Example 2 (2.95 kg in 11.5 L of water), 60 g of glutathione disulfide S-oxide obtained according to Example 1 was added at a temperature of 3-5 C, with thoroughly mixing for 5 minutes, the solution was left for 120 minutes at a temperature of 5° C., after which it was lyophilized.

Example 4. Preparation of the Composition (Drug) of Glutathione Disulfide with the Given Glutathione Disulfide S-Oxide Content 120 g of glutathione disulphide S-oxide prepared in accordance with Example 1 was added to glutathione disulfide disodium salt (2.95 kg in 11.5 L of water) prepared in Example 2 with thoroughly mixing for 5 minutes, the solution was left for 120 minutes at a temperature of 5 C, after which it was lyophilized.

Example 5. Preparation of the Composition of Glutathione Disulphide Disodium Salt with the Given Glutathione Disulphide S-Oxide Content To a suspension of 2760 g of reduced. L-glutathione in 7 L of water, 2245 g of 16% solution of sodium hydroxide was added with stirring at a temperature of not more than 17° C. After complete dissolution of glutathione, the mixture was cooled and 2546 g of 6% hydrogen peroxide was added at a rate of 30-50 ml/min with stirring at a reaction mass temperature of not more than +15° C. After peroxide addition, the resulting solution was stirred at a predetermined temperature for an additional 1 hour. After reaction completion (HPLC control), the reaction mass was cooled to 3° C. The chemical purity of the product, glutathione disulphide disodium salt was more than 98.5% (HPLC control).

Then additional 127 g of 6% hydrogen peroxide was added at a rate of 30-50 ml/min at a temperature not higher than +3° C. The reaction mass was allowed to stand for 1 hour at +3° C. and then lyophilized.

The resulting composition contains 95% of glutathione disulphide disodium salt and 4.5-5.0% of glutathione disulphide S-oxide disodium salt (HPLC control), which does not require procedures of additional purification of the product.

Example 6. Preparation of the Composition of Glutathione Disulphide with the Given Content of Glutathione Disulfide S-Oxide and Pt-S To a suspension of 2760 g of reduced L-glutathione in 7 L of water, 2245 g of 16% solution of sodium hydroxide was added at a temperature of not more than 17° C. After complete dissolution of glutathione, the mixture was cooled, 0.5 g of cis-platinum was added and 2546 g of 6% hydrogen peroxide was added with stirring at a rate of 30-50 ml/min at a temperature of the reaction mass not higher than +15° C. At the end of the peroxide addition, the resulting solution was stirred at a predetermined temperature for an additional 1 hour. After completion of the reaction (HPLC control), the solution containing 2.95 kg of glutathione disulphide disodium salt in 11.5 L of water was obtained which is cooled to 3° C. The chemical purity of the product, glutathione disulphide disodium salt was more than 98.5% (HPLC control), which does not require additional procedures for product isolation. The solution was cooled to 3° C. and 60 g of glutathione disulfide S-oxide was added, mixed thoroughly for 5 minutes, the solution was left for 120 minutes at 5° C., and then lyophilized.

Example 7. Analysis of the Folding Activity of the Composition Obtained in Example 5

The composition of the monoclonal antibody formulation:
monoclonal antibody—10 mg/ml;
glycine—2 mg/ml;
polysorbate 80-0.05 mg/ml;
sodium chloride—7 mg/ml;
citric acid monohydrate—2,101 mg/ml;
water for injection.

To reproduce the physiological conditions, the human blood serum was obtained with written voluntary consent. Serum number in the storage bank of sera is O-17-1002.

In the refolding experiment, the following were used:
Sample 1—composition of the formulation of monoclonal antibody in an amount of 50 μl+1 ml of serum O-17-1002.
Sample 2—composition of the formulation of monoclonal antibody+0.2 mM of the composition obtained in Example 3 in an amount of 50 μl+1 ml of serum O-17-1002.
Sample 3—composition of the formulation of monoclonal antibody+0.2 mM of the composition obtained in Example 4 in the amount of 50 μl+1 ml of serum O-17-1002.
Sample 4—composition of the formulation of monoclonal antibody+0.2 mM of the composition obtained in Example 5 in the amount of 50 μl+1 ml of serum O-17-1002.

The vials with samples 1 and 2 were stored at a temperature of 37° C. After 24 hours, the vials were removed from the the thermostats and analyzed for stability of the monoclonal antibody during storage at different temperatures under conditions of simulation of the physiological environment of the human body.

The results of the stability study were first analyzed by electrophoretic separation in a polyacrylamide gel (PAAG) under reducing conditions.

Electrophoresis was performed at 15% PAAG in denaturing conditions in an non-homogeneous (stepwise) buffer system (disk-electrophoresis) using the isotachophoresis (ITP) mechanism on the step of sample concentrating. Samples were prepared by the following method: the cells were precipitated by centrifugation and re-suspended in 200 µL of buffer (0.2 M Tris-HCl pH 7.5; 0.2 M NaCl; 0.01 M sodium acetate; 0.01 M b-mercaptoethanol and 5% glycerol) an then boiled for two minutes.

To carry out electrophoresis, system of several buffer solutions was used: cathode buffer was Tris base 0.1 M; Tricine 0.1 M; SDS 0.1% (terminal anion—tricine); anode buffer was Tris base 0.2 M pH 8.9 (lead anion—Cl⁻). Concentrating gel T=2.5-3%, separating gel with T=5-15% and C=2-5% (where T is the relative content of monomers in the gel, C is the content of the cross-linking agent in the sum of the monomers). Electrophoresis of cell lysates was carried out under denaturing conditions in 2% SDS.

The electrophoregram of protein preparations (FIG. 1) was analyzed using the ImageJ program. The program is designed for densitometric analysis of data from various experiments. Lanes were marked in the manual mode, then the bands corresponding to the proteins were marked within each of the lanes. The program evaluates the density of each of the bands, minus the background, which makes it possible to calculate the purity of the target protein.

HPLC Conditions for Studying the Structural Intermediates of the Monoclonal Antibody Arising from Storage Under Simulated Physiological Conditions.

Chromatograph Shimadzu LC-20 "Prominence"
Column Phenomenex "Jupiter" C18, 5 µm, 300 A, 250×4.6
Detection at the wavelength=210 nm
Injection volume=25 µl
Flow rate=1.0 ml/min
Column temperature=35° C.
Cell detector temperature=35° C.
Mobile Phase:
Eluent A. 30% acetonitrile+0.1% trifluoroacetic acid in water
Eluent B. 70% acetonitrile+0.1% trifluoroacetic acid in water
Runtime=47 min
Gradient Program:

| 0-1 min | 44% acetonitrile |
| 1-5 min | 48% acetonitrile |
| 5-20 min | 50% acetonitrile |
| 20-30 min | 53.4% acetonitrile |
| 30-35 min | 60% acetonitrile |
| 35-37 min | 60% acetonitrile |
| 37-40 min | 44% acetonitrile |
| 40-47 min | 44% acetonitrile |

Figure 2:
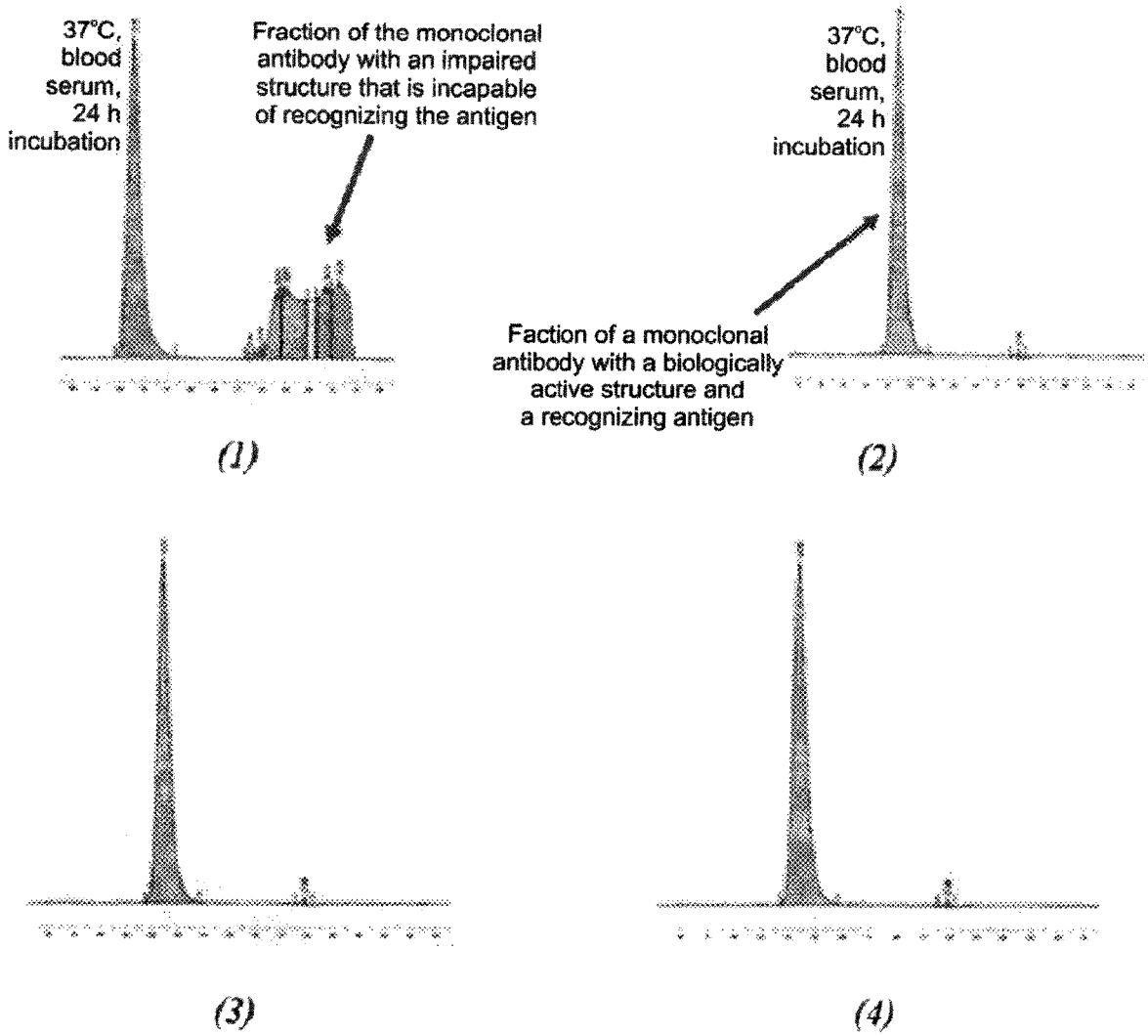
FIG. 2—HPLC data for structural intermediates of the monoclonal antibody arising from storage in blood serum samples under conditions simulating physiological ones ((1)—sample 1; (2)—sample 2; (3)—sample 3; (4)—sample 4).

The data obtained are shown in FIG. 2, which suggests that fraction of the monoclonal antibody with an impaired structure that is incapable of recognizing the antigen was absent in blood serum samples containing the compositions obtained according to Examples 3, 4, 5 (FIG. 2 (2), FIG. 2 (3), FIG. 2 (4), respectively), in contrast from the sample that does not contain said compositions (FIG. 2 (1)).

Example 8. The Combined Use of the Composition Comprising Glutathione Disulphide and Glutathione Disulfide S-Oxide in Combination with an Anticoagulant, Factor Xa Inhibitor Amidine Hydrochloride Composition obtained according to Example 3 of this application was studied for ability to enhance the therapeutic efficacy of the pharmacologically active agent amidine hydrochloride which is an anticoagulant, Factor Xa inhibitor. The test substance amidine hydrochloride (for example, obtained according to Example 2 in Patent EA 015918 B1, publ. 30 Dec. 2011) or mixture of amidine hydrochloride substance with an adjuvant (adjuvant was the composition obtained in Example 3 of this application) were administered intravenously with an insulin syringe 1 ml equipped with the 30 G needle in the lateral tail vein in the region ⅓ closer to the base of the tail. The individual dose volume for each animal was calculated based on the body weight and corrected after each weighing. The administration of substances was single. Said mixtures were prepared for intravenous administration of a mixture of amidine hydrochloride substance with an adjuvant to the animals. For this purpose, the amidine hydrochloride substance and adjuvant were dissolved separately in distilled water, and then the solutions were mixed. The solution was prepared immediately before administration to the animals and injected no later than 10 minutes after preparation. The volume of dose for rats was 0.31-0.42 ml.

Blood sampling was performed without anesthesia from the lateral tail vein above the site of intravenous administration (from ⅓ to ⅔ of the length of the tail), with preheating the tail of the rat for at least 15 minutes in a water bath with a temperature of 43° C. Blood volume 0.36 ml was taken with a 23 G needle into plastic tubes (such as Eppendorf) containing 0.04 ml of 0.11 M solution of sodium citrate to a volume of 0.4 ml, so that the ratio of sodium citrate solution to blood was 1:9. Within 30 minutes after sampling, the blood was centrifuged for 10 minutes at 8000 rpm (7000 g), the plasma was transferred to another tube and re-centrifuged at 12000 rpm (15000 g) at 20*C for 10 minutes to obtain a platelet-deficient plasma. The resulting plasma in a volume of 110 µl was poured into plastic tubes (such as Eppendorf) and frozen at −20° C. The sampling was performed 6 times in each rat.

The water-soluble, freeze-dehydrated thromboplastin with the addition of calcium ions, certified according to the International Sensitivity Index (ISI), Renamplastin (NPO "RENAM"), was used in the experiments.

The principle of the method: when an excess of tissue thromboplastin and calcium ions is added to the citrate plasma, the time for the formation of a fibrin clot depends only on the activity of factors of the external and general coagulation pathway: factors I, II, V, VII, X. The time from the moment of addition of thromboplastin with calcium to the plasma to fibrin clot formation is measured.

Assay: 8 ml of distilled water is added to the vial with lyophilized Renamplastin and dissolved with shaking. Before the assay, the reagent is heated at 37° C. for 30 minutes. 50 µl of citrate plasma is added to the cuvette of the analyzer, incubated at 37° C. for exactly 1-2 minutes. Then, 100 µl of renamplastin is added and the clotting time in seconds is recorded on the Merlin MC 1 Coagulogram Analyzer of ABW Medizin und Technik GmbH.

The results obtained are expressed as the International Normalized Ratio (INR):

$$INR=PR^{ISI},$$

where ISI is the International Sensitivity Index of Renamplastin, which should be indicated in the attached passport.
PR—prothrombin ratio:

$$PR=PT_B/PT_{100\%},$$

where $PT_B$ is the prothrombin time of plasma of the test sample in seconds, $PT_{100\%}$ is the average prothrombin time for the samples obtained for given animal before substance administration.

The results of measuring the study parameters were averaged over the experimental groups and are represented as M±m, where M is the group average, m is the standard deviation. The significance of difference between groups is determined using the Student's parametric t-test for $p<0.05$ for the normal sample distribution and the nonparametric Mann-Whitney U test for $p<0.05$ for an abnormal distribution.

Figure 3:
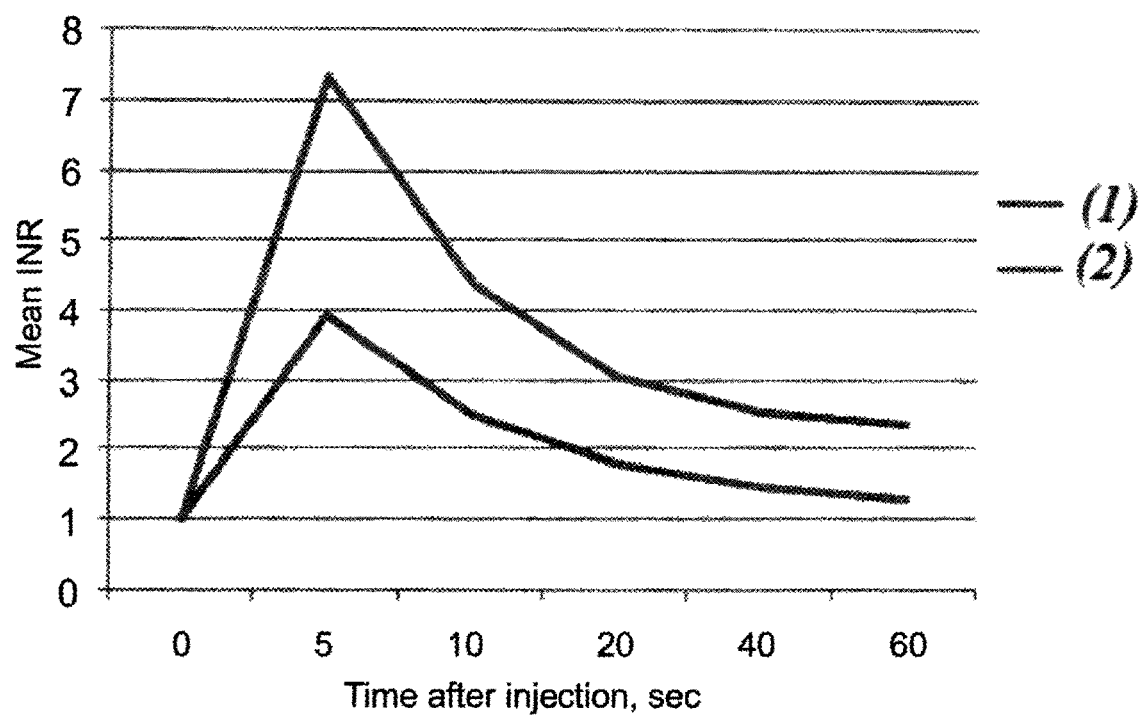
FIG. 3—Mean INR (1)—for the amidine hydrochloride substance obtained from Table 1, and (2)—for the mixture of the amidine hydrochloride substance and an adjuvant obtained from Table 2 (adjuvant is a composition comprising a combination of glutathione disulfide and glutathione disulphide S-oxide).

The results obtained are presented in Tables 1 and 2, and in FIG. 3. Table 1 and FIG. 3 (1) show the data obtained for amidine hydrochloride substance alone, and Table 2 and FIG. 3 (2) show the data obtained for the mixture of amidine hydrochloride substance and adjuvant.

TABLE 1

Results of the INR analysis with administration of amidine hydrochloride

| | | | Time after injection, sec | | | |
|---|---|---|---|---|---|---|
| | 0 | 5 | 10 | 20 | 40 | 60 |
| INR | 1 | 1.46 | 1.33 | 1 | 0.94 | |
| | 1 | 4.18 | 3.72 | 3.45 | 3.16 | |
| | 1 | 6.45 | 2.42 | 1.93 | 0.96 | |
| | 1 | 3.22 | 2.51 | 1.9 | 1.25 | |
| | 1 | 2.71 | 2.76 | 1.53 | 2.04 | |
| | 1 | 5.88 | 2.08 | 1.59 | 1.83 | 0.79 |
| | 1 | 9.82 | 1.18 | 2.94 | 1.74 | 1.63 |
| | 1 | 2.05 | 5.01 | 1.57 | 1.3 | 0.98 |
| | 1 | 2.42 | 5.53 | 1.85 | 1.8 | 1.43 |
| | 1 | 2.62 | 1.78 | 1.41 | 1.61 | 1.75 |
| | 1 | 2.13 | 2.15 | 1.68 | 1.05 | 1.24 |
| | 1 | 2.46 | 1.85 | 1.45 | 1.35 | 1.52 |
| | 1 | 2.3 | 2.21 | 2 | 1.44 | 1.65 |
| | 1 | 6.32 | 2.12 | 1.21 | 1.33 | 1.55 |
| | 1 | 4.85 | 2.23 | 1.75 | 1.48 | 1.38 |
| | 1 | 5.46 | 2.11 | 1.54 | 0.93 | 0.9 |
| | 1 | 2.63 | 2.23 | 1.79 | 1.31 | 1.24 |
| | 1 | | 1.72 | 1.61 | 1.21 | 0.96 |
| | 1 | | | | 1.15 | 1.07 |

TABLE 2

Results of analysis of INR values for combined use of amidine hydrochloride with adjuvant

| | | | Time after injection, sec | | | |
|---|---|---|---|---|---|---|
| | 0 | 5 | 10 | 20 | 40 | 60 |
| INR | 1 | 9.64 | 6.77 | 4.96 | 2.68 | 2.47 |
| | 1 | 10.38 | 5.21 | 4.26 | 2.38 | 1.92 |
| | 1 | 11.38 | 3.64 | 3.02 | 2.94 | 2.73 |
| | 1 | 4.53 | 4 | 2.44 | 1.63 | 1.84 |
| | 1 | 4.35 | 3.69 | 2.59 | 4.84 | 4.45 |
| | 1 | 6.84 | 3.9 | 2.09 | 2.28 | 1.59 |
| | 1 | 6.97 | 3.71 | 2.7 | 1.72 | 2.05 |
| | 1 | 4.69 | 4.17 | 2.29 | 1.72 | 1.96 |

The results obtained demonstrate the ability of the compositions of the present invention to enhance the efficacy of other therapeutically active agents.

Example 9: Study of Antimicrobial Activity of the Combination Comprising Moxifloxacin Combined with the Composition of Glutathione Disulphide and Glutathione Disulfide S-Oxide Formulations obtained according to the Examples 3, 4 and 5 of this application were studied.

Antimicrobial activity of the formulations was studied against Gram-negative: *Escherichia coli* ATCC 25923, *Pseudomonas aeruginosa* ATCC 27853, clinical isolate *Acinetobacter baumannii* and Gram-positive bacteria: *Listeria monocytogenes* EGD (ATCC BAA-679), *Staphylococcus aureus* ATCC 25922, MRSA ATCC 33591, which is methicillin-resistant *Staphylococcus aureus*.

Microorganisms were cultured overnight (16-18 hours) in 2.1% Mueller-Hinton broth M391 (Oxoid, Germany) at 37° C. with continuous shaking on a shaker. After this, aliquots of the bacterial suspension were removed from the overnight culture and transferred to 15 ml of fresh sterile 2.1% Mueller-Hinton broth, and then incubated at 37° C. on a shaker for 2.5-3 hours. Then, the optical density (OD) of the resulting suspension was measured on the DU-50 spectrophotometer (Beckman, USA) at the wavelength of 620 nm against the sterile 2.1% Mueller-Hinton broth and the number of colony forming units per ml (CFU) was determined by the formula: $1 \times OD620 = 2.5 \times 10^8$ cfu/ml [*Protocols in antimicrobial peptides*. W. Shafer Ed. Springer-Verlag New York, LLC, Jul. 8, 1997]. Based on this calculation, bacterial suspensions were diluted with sterile 2.1% Mueller-Hinton broth to a concentration of $1 \times 10^5$ cfu/ml.

96-well sterile U-bottomed plates were used (Sarstedt, Germany). Two-fold serial dilutions of the test formulations were prepared in the Müller-Hinton medium (8 dilutions for each formulation in a volume of 50 μl/sample). Further, 50 μl of the suspension of bacteria were added to the wells of the plates (final concentration of bacteria in the samples was $0.5 \times 10^5$ cfu/ml). Five duplicates were prepared for each dilution of the formulation.

Plates with samples were incubated in a thermostat at 37° C. for 18 hours.

The results were recorded the next day. The lowest concentration of the substance obtained, at which the growth of microorganisms in the corresponding wells of the plate was not visually observed (completely inhibited) was accepted as minimum inhibitory concentration (MIC). The final results were calculated on the basis of data from 5 independent experiments, each of which had 5 duplicates for each dilution of each of the samples tested.

Antimicrobial activity (AMA) of formulations was also determined by radial diffusion in agarose gel containing test microorganisms developed by prof. Lehrer, University of Los Angeles, USA [Lehrer R. L et al. *Ultrasensitive assays for endogenous antimicrobial polypeptides/Journal of Immunological Methods*, 1991, V. 137, pp. 167-173]. Microorganisms were pre-cultured for 16 hours in the medium representing a 3% solution of soybean tryptic hydrolysate at 37° C. Aliquots of media with microbes were then transferred separately to the freshly prepared medium and incubated at 37° C. for 2.5 hours to obtain microorganisms in the middle of the logarithmic growth phase. The number of cells of each of the microorganisms was evaluated by measuring the optical density of the suspensions on a spectrophotometer at 620 nm. Aliquots of the suspensions containing $4 \times 10^6$ cells of microorganisms are mixed with 10 ml of sterile 1% agarose solution in 10 mM sodium phosphate buffer, pH 7.4, containing 0.15 M NaCl at a temperature of 42° C. The resulting mixture is poured into sterile plastic Petri dishes with a diameter of 90 mm and left at room temperature until solidified. Analyzed samples representing successive dilutions of the formulations in 10 mM sodium phosphate buffer, pH 7.4, in a volume of 5 μl, were added to the wells made by the applicator (diameter 3 mm) and incubated in an air thermostat for 3 hours at 37° C. Then 1% agarose containing 6% TGS is poured into the plates and incubated for 18 hours at 37° C. The diameter of the growth inhibition zone (zone around the well, free of microorganisms) is measured by taking 1 conventional unit of antimicrobial activity of 0.1 mm and subtracting from the measured value 30 conventional units corresponding to the diameter of the well itself. The concentrations of formulations used were 64 μg/ml, 32 μg/ml, 16 μg/ml, 8 μg/ml, 4 μg/ml, 2 μg/ml, 1 μg/ml.

The minimum concentrations inhibiting the growth of microorganisms (MIC) of formulations are determined by constructing linear regressions of the dependence of antimicrobial activity on the concentration of peptides: y=a+bx, where y is the antimicrobial activity (c.u.), and x is the concentration of the formulation. The MIC was taken to be the value of x for y=0, i.e. MIC=−a/b.

TABLE 3

Minimum inhibitory concentrations of peptides, in μg/ml, for *Escherichia coli* ATCC 25922[#] (serial dilution method in liquid culture medium)

| Formulation | Bacteria MIC, μg/ml | | | | | |
|---|---|---|---|---|---|---|
| | Exp. 1 | Exp. 2 | Exp. 3 | Exp. 4 | Exp. 5 | mean ± SE |
| No. 1 (according to Example 3) | 0.25; 0.25; 0.25; 0.25; 0.25 | 0.25; 0.25; 0.25; 0.5; 0.25 | 0.25; 0.25; 0.25; 0.5; 0.25 | 0.25; 0.25; 0.25; 0.5; 0.25 | 0.5; 0.5; 0.5; 0.5; 0.5 | 0.33 ± 0.02 |
| No. 2 (according to Example 4) | 0.25; 0.25; 0.25; 0.25; 0.25 | 0.25; 0.25; 0.25; 0.25; 0.5 | 0.5; 0.5; 0.5; 0.5; 0.25 | 0.25; 0.25; 0.25; 0.25; 0.25 | 0.5; 0.5; 0.5; 0.5; 0.5 | 0.35 ± 0.03 |
| No. 3 (according to Example 5) | 0.25; 0.5; 0.5; 0.5; 0.5 | 0.25; 0.25; 0.25; 0.25; 0.25 | 0.25; 0.25; 0.25; 0.25; 0.25 | 0.25; 0.25; 0.25; 0.25; 0.25 | 0.25; 0.25; 0.25; 0.5; 0.5 | 0.31 ± 0.02 |

[#]Each of the presented values is the mean ± standard error of the mean (n = 25).

TABLE 4

Minimum inhibitory concentrations of peptides, in μg/ml, for *Staphylococcus aureus* ATCC 25923[#] (serial dilution method in a liquid culture medium)

| Formulation | Bacteria MIC, μg/ml | | | | | |
|---|---|---|---|---|---|---|
| | Exp. 1 | Exp. 2 | Exp. 3 | Exp. 4 | Exp. 5 | mean ± SE |
| No. 1 (according to Example 3) | 0.5; 0.5; 0.5; 0.5; 0.5 | 0.5; 0.5; 0.5; 0.5; 0.5 | 0.25; 0.25; 0.25; 0.5; 0.25 | 0.5; 0.25; 0.25; 0.25; 0.25 | 0.25; 0.25; 0.25; 0.5; 0.25 | 0.38 ± 0.03 |
| No. 2 (according to Example 4) | 0.25; 0.25; 0.25; 0.25; 0.25 | 0.5; 0.5; 0.5; 0.5; 0.5 | 0.25; 0.25; 0.25; 0.25; 0.5 | 0.25; 0.25; 0.25; 0.25; 0.25 | 0.25; 0.25; 0.25; 0.25; 0.25 | 0.31 ± 0.02 |
| No. 3 (according to Example 5) | 0.25; 0.25; 0.25; 0.25; 0.25 | 0.5; 0.5; 0.5; 0.5; 0.5 | 0.25; 0.25; 0.25; 0.25; 0.25 | 0.25; 0.25; 0.25; 0.25; 0.25 | 0.25; 0.25; 0.25; 0.5; 0.5 | 0.32 ± 0.22 |

[#]Each of the presented values is the mean ± standard error of the mean (n = 25).
*Significant difference against moxifloxacin MIC (No. 13), Student's t-test.

The studies conducted demonstrate the high antimicrobial activity of the compositions of the present invention against both Gram-negative and Gram-positive bacteria.

Example 10. Use of the Composition Obtained in Example 3 Containing Glutathione Disulphide and Glutathione Disulphide S-Oxide as Adjuvant in Vaccine Formulation Preparation of combination of dry concentrated purified inactivated cell-derived anti-rabies vaccine and a composition according to Example 3 of this application.

Sterile 0.5 mg/ml solution of aluminum hydroxide in PBS was prepared. 12 g of the composition obtained according to Example 3 of this application were added to 60 ml of the resulting solution. The resulting solution was sterilized by passing through a filter with a pore diameter of 0.44 μm. Diluted solutions (AD) at a concentration of 20 mg/ml, 10 mg/ml, 5 mg/ml, 1 mg/ml in PBS at a concentration of 0.5 mg/ml of aluminum hydroxide were prepared from the resulting solution.

The solutions obtained were used for preparation of vaccines with 1:200 (calculated 50% protection of mice) and 1:1200 (calculated 20% protection of mice) dilution in the solution with the predetermined concentration of the substance according to Example 3 (present application) in PBS with 0.5 mg/ml aluminum hydroxide. The resulting solutions were incubated at 4° C. for 1 hour on a shaker (about 150 rpm), not allowing foaming.

Dry concentrated purified inactivated cell-derived anti-rabies vaccine with a dilution of 1:200 and 1:1200 was used as a reference sample.

The BALB/s mice weighing 13-15 g of one supply were used as the object of the study.

The working dilution containing 20 to 100 $LD_{50}$ in 0.03 ml was calculated based on the results of titration of the CVS test strain of the rabies virus (10% brain suspension of mice infected with the rabies virus).

The first immunization of mice was performed intraperitoneally by 0.5 ml from the calculation of 10 heads for each dilution of the composition.

The second immunization of mice after 7 days intraperitoneally with 0.5 ml from the calculation of 10 heads for each dilution of the composition.

Preparation of the working (permissive) dilution of virus and three consecutive tenfold dilutions in water for injection with the addition of 2% of horse's serum, inactivated at 56° C. for 30 minutes, to determine the actual dose of the virus taken in the experiment.

Permissive dose of 0.03 ml and its decimal dilutions were administered intracerebrally to control group of mice concurrently with immunized mice using 6 mice per dilution.

Follow-up period of the animals was 14 days. Evaluation of the results of the experiment takes into account mice that fell ill or died from 5 to 14 days.

The mathematical processing of the results by the Reed-Muench method.

The results obtained are summarized in Table 5.

TABLE 5

Results of the influence of the adjuvant on the efficacy of the vaccine formulation

| Name of the administered material | Vaccine (1:200) | | Vaccine (1:1200) | | MLT |
|---|---|---|---|---|---|
| | live | % of protection | live | % of protection | |
| Vaccine (1:70) with AD 1 mg/ml | 10/10 | 100% | 6/10 | 60% | 12.8 days |
| Vaccine (1:200) with AD 5 mg/ml | 10/10 | 100% | 1/10 | 10% | 12.8 days |
| Vaccine (1:70) with AD 10 mg/ml | 8/10 | 80% | 5/10 | 50% | 10.7 days |
| Vaccine (1:200) with AD 20 mg/ml | 10/10 | 100% | 2/10 | 20% | 11.2 days |
| Vaccine without AD | 7/10 | 70% | 3/10 | 30% | 12.8 days |
| St. CVS | — | — | — | — | 5.5 days |

The data presented indicate a high survival rate for animals when the vaccine containing the combination of glutathione disulphide and glutathione disulphide S-oxide is administered. These values are comparable, and in most cases even higher than those of the reference sample (for the cell-derived anti-rabies vaccine).

Example 11. Effect of the Composition Comprising Glutathione Disulfide and Glutathione Disulfide S-Oxide Obtained According to Example 3 on the Activity of Calcium Channel Inhibitors The aim of the study is to test the effect of the composition obtained in Example 3 of this application on the activity of the cell membrane ion channels and the activity of calcium channel inhibitors.

The following compounds were used as test compounds: selective calcium channel inhibitor nifedipine, glutathione disulfide (prepared in Example 2 of this application), and the composition according to Example 3 of this application (comprising glutathione disulphide together with glutathione disulfide S-oxide).

Preparation of Formulations for the Study:

The test compounds and compositions were stored at +4° C.; the substances were dissolved in deionized water (super Q) immediately before the start of the experiment. The prepared solution was stored at +4° C. for no more than 5 hours. The compounds were added to the cell culture medium to the final concentration to be studied.

The formulation was added to the cells once for the indicated time period.

Cell Line Used, Cultivation Conditions:

The experiments were performed on cultured resident peritoneal rat macrophages.

Resident macrophages were isolated from the peritoneal cavity of rats weighing 200-300 g by the method described earlier in [Conrad R. E. *Induction and collection of peritoneal exudate macrophages. Manual of macrophages methodology*/New York: Marcell Dekker.—pp. 5-11; Randriamampita C. et al. *Ionic channels in murine macrophages*/ Cell Biology, 1987, V. 105, pp. 761-769]. Immediately after isolation, the cells had a spherical shape and a diameter of 10-20 μm. The cell suspension was placed on culture dishes containing quartz glasses 10×10 mm. Cells on glasses were cultured in medium 199 (pH 7.2) with the addition of 20% bovine serum, glutamine solution (3%), penicillin (100 U/ml) and streptomycin (100 mg/ml) for 1-3 days at 37° C. α-naphthyl acetate esterase staining [Monahan R. A. et al. *Ultrastructural localization of nonspecific esterase activity in guinea pig and human monocytes, macrophages and lymphocytes*/Blood, 1981, V. 58, pp. 1089-1099] determined that at least 96% of the cells in the monolayers were macrophages. Experiments were carried out at room temperature 20-22° C. on 2-3 days of cell cultivation.

Quartz glasses with cells were placed in the experimental chamber filled with the physiological solution of the following ionic composition (mM): NaCl—140, KCl—5, $CaCl_2$—1, $MgCl$—1, HEPES-NaOH—5; pH 7.3-7.4 (Alonso-Torre, *Trautmann*, 1993). The calcium-free medium contained 0 mM $CaCl_2$ and 1 mM EGTA.

Reagents from Sigma were used in the experiments. Stock solutions of thapsigargin (500 μM), nifedipine (20 mM) were prepared in dimethylsulfoxide. Stock solutions of glutathione disulphide and the composition according to Example 3 (0.45 μmol/ml), ATP (100 mM) were prepared in water.

Experiment Mode:

To measure the intracellular calcium concentration ($[Ca^{2+}]_i$), a Fura-2AM fluorescent probe was used. The macrophages were incubated for 45 minutes in saline containing 2 μM Fura-2AM at room temperature (to prevent endocytosis of Fura-2AM micelles that occurs at 37° C.) [Alonso-Torre S. R. et al. *Calcium responses elicited by nucleotides in macrophages. Interaction between two receptor subtypes*/The Journal of Biological Chemistry, 1993, V. 268, pp. 18640-18647].

The glasses with the colored cells were washed with saline and transferred to the experimental chamber located on the table of the luminescent microscope "Люмам-КФ". Fluorescence of Fura-2 was excited at 337 nm with a nitrogen laser ЛГИ-503. The laser was placed alongside of the microscope at the angle of 30° to the experimental chamber, which allows to direct the laser beam directly to the object. The intensity of fluorescence was recorded using the spectrophotoheader СФН-10 at 510 nm. The signal from ФЭУ-79 was amplified with the specially designed amplifier and recorded on the computer IBM PC using original software. A lens 10×0.40 was used in the experiments. At a given magnification, 40-50 cells enter the area of the photometric region. In order to avoid photo-burning, measurements are taken every 20 seconds with the object irradiation of 2.5 sec. When ATP and UTP are added, the cells are irradiated continuously until a maximum of fluorescence is reached. The values of $[Ca^{2+}]_i$ are calculated from the Grynkiewicz equation [Grynkiewicz G. et al. *A new generation of $Ca^{2+}$ indicators with greatly improved fluorescence properties*/The Journal of Biological Chemistry, 1985, V. 260, pp. 3440-3450]:

$$[Ca^{2+}]_i = K_d \times (F - F_{min})/(F_{max} - F),$$

where F is the observed intensity of the fluorescence; $F_{max}$ is the fluorescence of the dye saturated with $Ca^{2+}$; $F_{min}$ is the fluorescence of the dye free of $Ca^{2+}$ (in a calcium-free medium).

The dissociation constant, $K_d$ of the Fura-2AM:$Ca^{2+}$ complex is 135 nM at 20° C. and pH 7.1-7.2, $F_{max}$ was measured after the addition of 10 μM Ionomycin or 25 μM digitonin to the cells in a medium containing $Ca^{2+}$. Treatment of cells with digitonin allows $Ca^{2+}$ ions to freely penetrate through the plasma membrane, without affecting the permeability of mitochondrial membranes and endoplasmic reticulum. After stabilizing the signal, 5 mM EGTA was added and the fluorescence of the dye is determined in the nominally calcium-free medium ($F_{min}$). The level of intrinsic fluorescence was subtracted after the addition of the solution of $MnCl_2$ (100 μM) to the macrophages. $Mn^{2+}$ displaces $Ca^{2+}$ from the complex with Fura-2, and the fluorescence of the dye complex with $Mn^{2+}$ is 100 times lower than the fluorescence of the Fura-2 complex with $Ca^{2+}$. For Fura-2, $F_{min} = F_{max}/3$.

Two experimental approaches were used in the studies. In the first, the effect of pharmacological agents on the $Ca^{2+}$ response caused by ATP, UTP, thapsigargin, or cyclopyasonic acid (CPC) in macrophages in normal saline was investigated. The agents were administered either before the action of the agonists, or after, during the plateau phase of the $Ca^{2+}$-signal reflecting the entry of $Ca^{2+}$ from the external medium. In the second variant of experiments, the following experiment scheme ($Ca^{2+}$-free/$Ca^{2+}$-reintroduction protocol) was used to detect and enhance the entry of $Ca^{2+}$ into cells. The macrophages were incubated in a nominally calcium-free medium, then they were exposed to one of the agonists, causing mobilization of $Ca^{2+}$ from the intracellular depot. After the addition of 2 mM $Ca^{2+}$ to the external medium and the restoration of the physiological gradient of $Ca^{2+}$ concentration, a rapid increase of $[Ca^{2+}]_i$, reflecting the entry of $Ca^{2+}$ into the cell, was observed. Further, the effect of pharmacological agents added prior to the administration of agonists was investigated prior to administration of $Ca^{2+}$ or during the developing entrance of $Ca^{2+}$ from the external environment.

The Results of the Effect of the Test Compounds on the Intracellular Concentration of $Ca^{2+}$ and $Ca^{2+}$-Signals Induced by ATP and Thapsigargin in Rat Macrophages.

Figure 4:
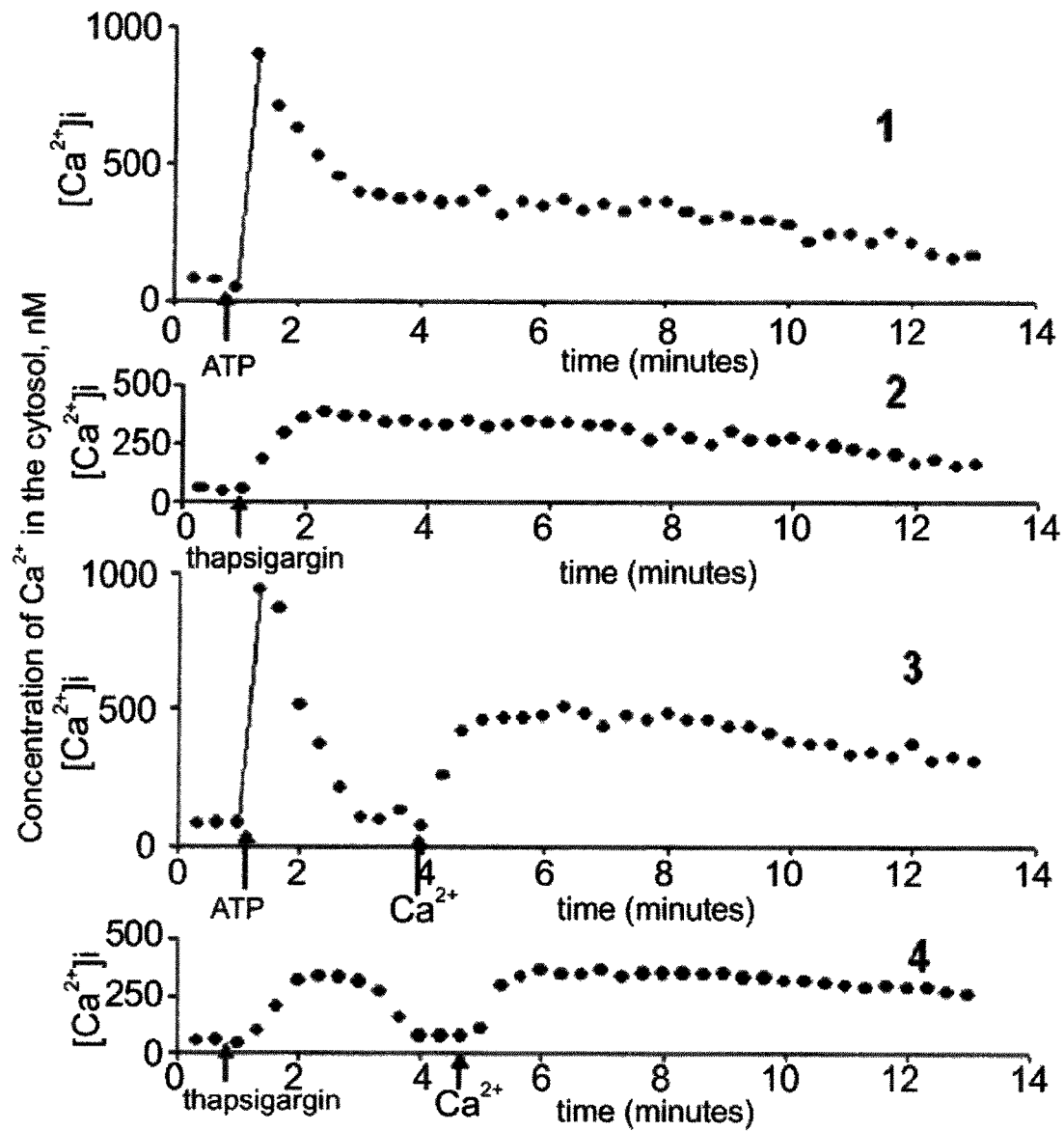
FIG. 4—$Ca^{2+}$-signals induced by ATP (1), (3) and thapsigargin (2), (4) in peritoneal macrophages in a medium containing $Ca^{2+}$ ions (1), (2) and in a calcium-free medium (3). (4). Vertically—concentration of $Ca^{2+}$ in the cytosol, nM. Horizontally—time in minutes.

Addition of 200 μM ATP to the medium of incubation of rat peritoneal macrophages causes a two-phase $Ca^{2+}$ signal consisting of an initial short-term peak associated mainly with the mobilization of $Ca^{2+}$ from the depot caused by $P_{2u}$ receptor activation and a pronounced prolonged "plateau" phase. This plateau phase is caused by the entry of $Ca^{2+}$ from the external medium and presumable reflects the simultaneous activation of $P_{2u}$ and $P_{2z}$ receptors. FIG. 4 (1) shows the characteristic $Ca^{2+}$-signal induced by extracellular ATP (200 μM) in the population of 40-50 macrophages in normal saline.

In response to the adding of extracellular ATP $[Ca^{2+}]_i$ increases from the basal level of 75±18 nM to peak 820±105 nM. Then the slowly decreasing phase of the plateau follows, during which average $[Ca^{2+}]_i$ is 460±115 nM 4 minutes after the addition of ATP.

A specific inhibitor of endoplasmic $Ca^{2+}$-ATPases thapsigargin (0.5 μM) also causes a two-phase $Ca^{2+}$-signal: peak associated with the mobilization of $Ca^{2+}$ from the depot, which is quite fast, and a long phase reflecting the depot-dependent entrance of $Ca^{2+}$ from the external environment. FIG. 4 (2) presents the typical $Ca^{2+}$-signal induced by thapsigargin in macrophages in normal saline.

Experiments using calcium-free medium were performed to identify and enhance the phase of $Ca^{2+}$ entry into the cell. After stimulation of macrophages with 200 μM ATP (FIG. 4 (3)) or 0.5 μM thapsigargin (FIG. 4 (4)) in the nominally calcium-free medium (0 mM $CaCl_2$ and 1 mM EGTA), the $Ca^{2+}$ entry was induced by adding 2 mM $Ca^{2+}$ into the external environment.

Figure 5:
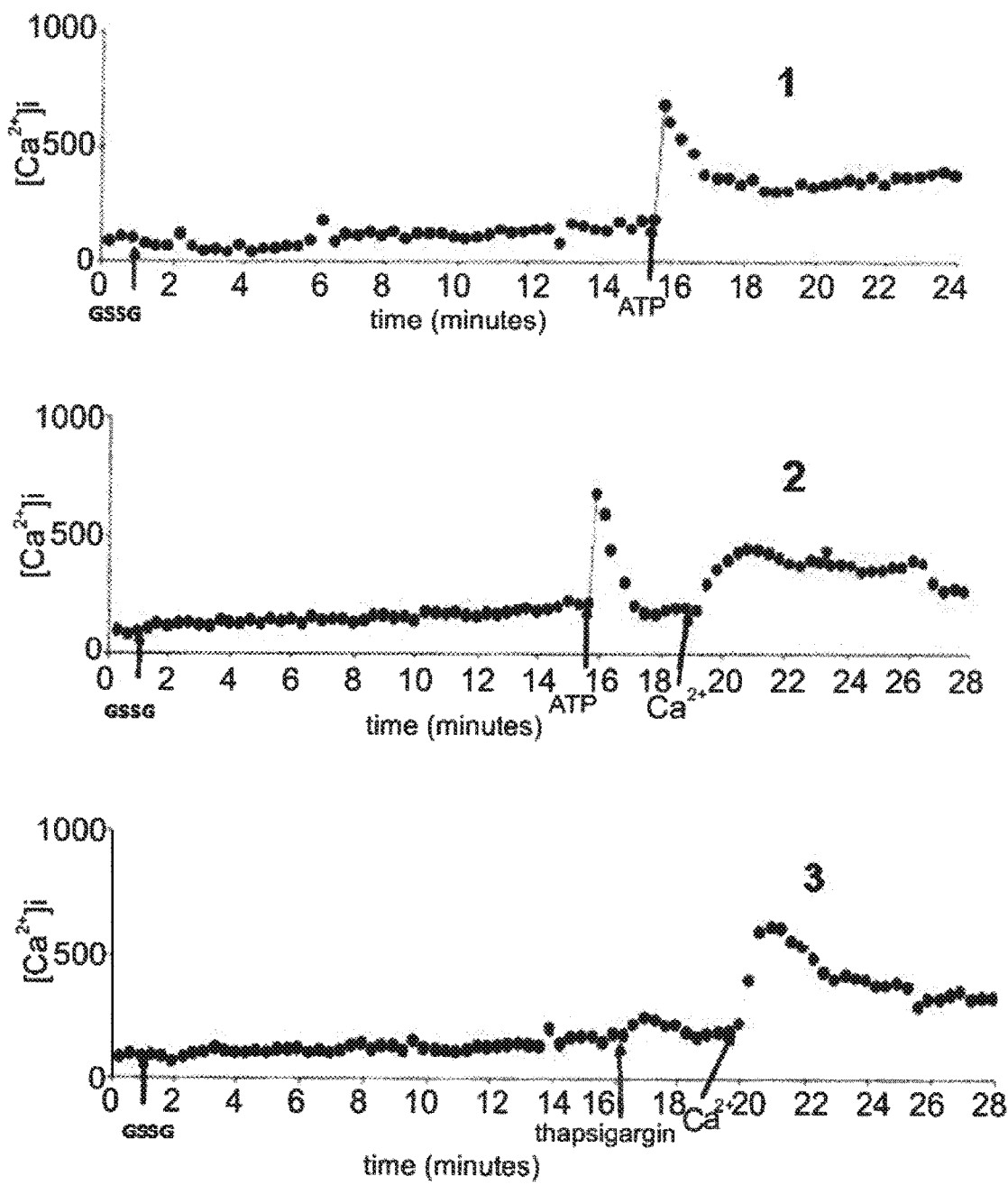
FIG. 5—Effect of glutathione disulfide on $[Ca^{2+}]_i$ at rest and $Ca^{2+}$-signals induced by 200 μM ATP (1, 2) and 0.5 μM of thapsigargin (TG) (3) in macrophages in normal saline (1) or in a nominally calcium-free medium (2), (3).

FIG. 5 shows the effect of glutathione disulfide on $[Ca^{2+}]_i$ at rest and $Ca^{2+}$-signals induced by 200 μM ATP (1), (2) and 0.5 μM thapsigargin (3) in macrophages in normal saline (1) or in nominally calcium-free medium (2), (3).

The data obtained indicate the ability of glutathione disulfide to increase $[Ca^{2+}]_i$ to 180±19 nM due to the mobilization of calcium from the intracellular depot. The devastation of intracellular calcium depot reduces the effect of ATP. Thapsigargin completely reverses the effect of the ability of glutathione disulphide to mobilize calcium from the depot.

Figure 6:
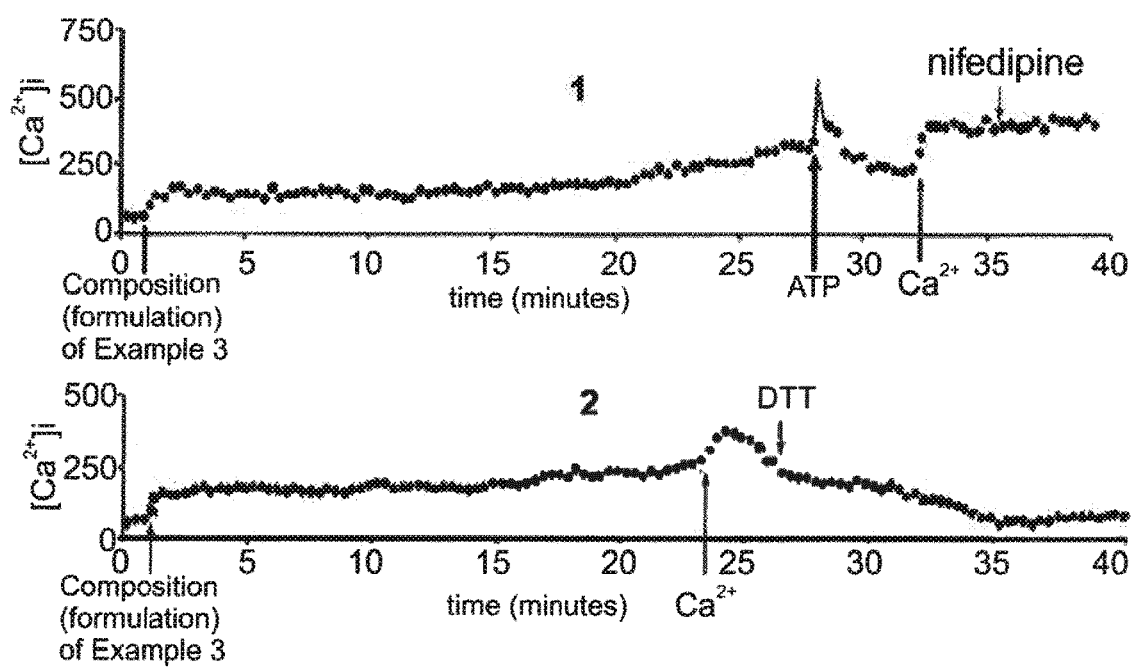
FIG. 6—Effect of the composition (formulation) of Example 3 on the intracellular calcium concentration $[Ca^{2+}]_i$ at rest and $Ca^{2+}$-signals caused by ATP. The formulation negates the inhibitory effect of the selective calcium channel inhibitor nifedipine (1), wherein the effect of the drug itself is suppressed by the reducing agent dithiothreitol (DTT) (2).

FIG. 6 shows the effect of the composition (formulation) according to Example 3 of this application on the intracellular calcium concentration $[Ca^{2+}]_i$ at rest and $Ca^{2+}$-signals induced by ATP. The formulation negates the inhibitory effect of the selective calcium channel inhibitor nifedipine (1), wherein the effect of the formulation itself is suppressed by reducing agent dithiothreitol (2).

The data obtained indicate the ability of glutathione disulfide together with glutathione disulfide S-oxide to increase $[Ca^{2+}]_i$ up to 240±28 nM due to mobilization of calcium from the intracellular depot. The devastation of intracellular calcium depot reduces the effect of ATP. Glutathione disulfide together with glutathione disulfide S-oxide stabilizes the process of calcium supply to the cell from the medium, which is exhibited as suppression of the effect of the calcium channel inhibitor nifedipine on this process. Dithiothreitol negated the stabilizing effect of glutathione disulfide together with glutathione disulfide S-oxide on the performance of calcium channels.

Thus, glutathione disulfide S-oxide is able to enhance the effect of certain compounds on cells, in the experiment conducted it was the glutathione disulphide with respect to which glutathione disulfide S-oxide acted as a synergist. Glutathione disulfide S-oxide in conjunction with glutathione disulfide can reduce or inhibit the effect of other compounds (in the experiment conducted it was nifedipine), toward that the composition acts as an antagonist and a remedy neutralizing the toxicity of nifedipine.

The results of the examples presented show that glutathione disulfide in conjunction with glutathione disulfide S-oxide exhibits high biological activity, which is exhibited as an increase in the mobilizing calcium activity by 30-50%. Taking into account the ability of glutathione disulfide to modulate the activity of surface-cell receptors and ion channels, it points at the ability to influence extracellular and intracellular receptors, carrier proteins of cytoplasmic and intracellular membrane, extracellular regulatory and transport molecules of peptide nature, cytoskeleton proteins, autoimmune reactions; antigen binding and recognition, processes of exo- and endocytosis, chemotaxis, chemokinesis, cytokinesis; intercellular, matrix cellular and humoral cell interactions; it can be assumed that disulfide S-oxide will act as a synergist in these effects of glutathione disulfide, which can be used in the developing of new drugs, the possibility of using at lower doses without loss of therapeutic effectiveness, and a reducing variety of dose-dependent toxic and side effects.

Example 12. Effect of Composition Obtained in Example 5 by the Rate of Formation of the Disulfide Bond A 1 g sample obtained according to Example 5 (glutathione disulfide S-oxide content 5%) was dissolved in water (9 ml). To the resulting solution, 1 ml of the solution of sodium salt of reduced L-glutathione (2.5 mg/ml) was added with stirring. The reaction mass was stirred for 5 minutes and analyzed by HPLC. Glutathione disulfide S-oxide was not detected in the resulting solution.

Example 13. Effect of the Composition Comprising Glutathione Disulfide S-Oxide with Glutathione Disulfide and Metal, Platinum Compound Pt-S Cisplatin, Obtained According to Example 6 on the Expression of the Enzymes of the Second Phase of Xenobiotic Detoxification As the test compounds are used:
1—glutathione disulfide S-oxide (compound obtained in Example 1);
2—glutathione disulfide (compound obtained in Example 2);
3—composition of glutathione disulfide S-oxide with glutathione disulfide (composition obtained in Example 5);
4—composition of glutathione disulfide S-oxide with glutathione disulfide and metal, platinum compound Pt-S cisplatin (composition obtained in Example 6).

The study was carried out on random bred white male rats weighing 140-160 g, from breeding ground RAMS "Rappolovo" hepatotoxicity in which was caused by daily administration of cyclophosphan (CP) at a dose of 20 mg/kg s.c. in the saline for 10 days.

6 groups of experimental animals were formed.
No. 1—intact animals receiving injections of solvent of the studied compounds (saline) (solvent control);
No. 2—animals receiving CP and then saline as a therapeutic agent (control);
Experimental Groups:
No. 3—animals receiving test compound 1 in saline intraperitoneally at a dose of 10 mg/kg 30 minutes after the administration of the toxic agent CP for 10 days;
No. 4—animals receiving test compound 2 in saline intraperitoneally at a dose of 0.1 mg/kg 30 minutes after the administration of the toxic agent CP for 10 days;
No. 5—animals receiving the test composition 3 in saline intraperitoneally at a dose of 10 mg/kg 30 minutes after the administration of the toxic agent CP for 10 days;
No. 6—animals receiving the test composition 4 in saline intraperitoneally at a dose of 10 mg/kg at 30 minutes after administration of the toxic agent CP for 10 days.

The enzymes of the second phase of xenobiotic detoxification in the cytosolic fraction of liver cells: glutathione-S-transferase (XE 2.5.1.18), glutathione peroxidase (XE 1.11.1.9), glutathione reductase (XE 1.6.4.2) glucose-6-phosphate dehydrogenase (XE 1.1.1.49).

Study Results

The results of the study of a complex of molecular reactions providing for tolerance to the action of toxic substances, indicate the ability of glutathione disulfide S-oxide (1), glutathione disulfide (2), compositions thereof (3 and 4) to induce the activity of enzymes of the second phase of xenobiotic detoxification glutathione reductase (XE 1.6.4.2), glutathione peroxidase (XE 1.11.1.9), glutathione-S-transferase (XE 2.5.1.18) and exchange of reduced glutathione associated with them (Table 6).

TABLE 6

Change of activity of the enzymes of the second phase of xenobiotic detoxification in liver cells of random bred white rats on repeated administration of cyclophosphan at a dose of 20 mg/kg for 10 days

| Study group | Values of the analyzed parameter | | | | |
|---|---|---|---|---|---|
| | GR | GP | GST | G-6-PDG | GSH |
| Control | 371.3 ± 15.8 | 71.2 ± 0.4 | 2281 ± 187 | 181.6 ± 12.9 | 23.68 ± 0.62 |
| Uncorrected | 95.3 ± 11.7* | 13.8 ± 0.2 | 1727 ± 86* | 86.2 ± 7.7* | 9.61 ± 0.02* |
| No1 (GS(O)SG, compound according to Example 1) | 117.8 ± 12.6** | 27.9 ± 2.2** | 1857 ± 120** | 98.1 ± 13.3** | 11.21 ± 0.56** |
| No2 - (GSSG, compound according to Example 2) | 125.6 ± 11.2** | 24.5 ± 3.1** | 1794 ± 165** | 96.9 ± 18.7** | 12.93 ± 1.15** |
| No3 (GSSG + GS(O)SG, composition according to Example 5) | 237.4 ± 23.1** | 48.3 ± 5.9** | 2117 ± 223** | 133.1 ± 21.2** | 17.87 ± 2.12** |
| No4 - (GSSG + GS(O)SG + Pt—S, composition according to Example 6) | 394.7 ± 37.4** | 83.9 ± 7.1** | 2310 ± 343** | 189.7 ± 29.3** | 36.12 ± 5.07** |

*reliability of the difference $p < 0.05$ versus control group;
**reliability of the difference $p < 0.05$ versus group of poisoned animals, uncorrected;
GR - glutathione reductase (ХЕ 1.6.4.2);
GP - glutathione peroxidase (ХЕ 1.11.1.9);
GST - glutathione-S-transferase (ХЕ 2.5.1.18);
G6PDG - glucose-6-phosphate dehydrogenase (ХЕ 1.1.1.49);
GSH - reduced glutathione
(Enzyme activity in μmol/(min × g protein, reduced glutathione – μmol/g protein) under the action of the test substances: 1 - glutathione disulfide S-oxide; 2 - glutathione disulphide; 3 - composition of glutathione disulfide S-oxide with glutathione disulphide (composition obtained in Example 5); 4 - composition of glutathione disulfide S-oxide with glutathione disulphide and metal, platinum compound Pt—S cisplatin (composition obtained in Example 6)

Adding metal compounds, especially compounds of platinum Pt-S, to the composition enhanced the ability of the composition of glutathione disulfide and glutathione disulfide S-oxide to induce activity of the enzyme of the second phase of xenobiotic detoxification, increased the intensity of the exchange of key metabolite of reduced glutathione associated with them.

Thus, metal compound, in particular the compounds of platinum Pt having the ability to induce the activity of the enzymes of the second phase of xenobiotic detoxification, increase its toxicomodifying and, consequently, cytoprotective effect due to inducing the enzymes of the second phase of xenobiotic detoxification by composition of glutathione disulfide S-oxide and glutathione disulphide.

Example 14. Effects of Glutathione Disulfide S-Oxide and Compositions Thereof on the Antiviral Efficacy of Interferon α

Study of the effect of glutathione disulfide S-oxide and compositions thereof (Examples 1, 2, 5, 6) on the antiviral activity of interferon is carried out on the culture of infected cells.

The method for evaluating the antiviral activity of interferon is based on the determination of its minimum amount that protects cells of the Л-68 line from cytopathic action of the virus. The compositions are added to the cell incubation medium to a concentration of 0.0015 μmol/ml, 0.015 μmol/ml, and 0.15 μmol/ml before interferon adding, together with interferon, and 10 min, 30 min and 60 min after adding of interferon. The interferon titer in the experiments was $4 \times 10^{-4}$ U/ml, $8 \times 10^{-4}$ U/ml, $1.6 \times 10^{-5}$ U/ml, $3.2 \times 10^{-5}$ U/ml, $6.4 \times 10^{-5}$ U/ml, $1.28 \times 10^{-6}$ U/ml, $2.56 \times 10^{-6}$ U/ml, $5.12 \times 10^{-6}$ U/ml. The antiviral activity of the formulations was evaluated by the ability of living cells to absorb crystal violet. The amount of crystal violet absorbed was determined photometrically at 595 nm, after separation of the living cell fraction and extraction of the dye with methanol. The amount of absorbed dye was proportional to the number of living cells and expressed in terms of optical density.

Prepare the Л-68 Cell Line for the Experiment.

The Л-68 cell line is a strain of diploid cells of the human embryonic lung obtained from the Moscow Research Institute of Viral Preparations (MRIVP) of the Russian Academy of Medical Sciences (RAMS) from lung cells of the human embryo at the age of 11 weeks aborted from the woman at the age of 28 years who hadn't oncological, venereal diseases, hepatitis, tuberculosis, genetic and congenital anomalies.

Seed bank of the strain of diploid cells Л-68 is certified for the preparation of immunobiological preparations in MRIVP RAMS together with State Scientific Research Institute for Standardization and Control of Medical Biological Preparations named after L. A Tarasevich (SISC).

Cell of Л-68 line were cultivated at 37° C. in complete growth medium I. Cultivation is carried out in 250 ml plastic vials ("Costar" type). The cells covered the bottom of the vial, forming a monolayer with the morphology typical for diploid fibroblasts. The flatted cells were suspended using special medium consisting of equal parts of 0.02% Versene's solution and 0.25% solution of trypsin. To do this, a complete growth medium was drained from the vial with a formed monolayer of cells, the monolayer was washed twice with the special medium (Versene's solution with trypsin) and incubated at 37° C. for 5 minutes. During this time, the monolayer of fibroblasts was detached from the plastic. The detached cells were diluted with complete growth medium, breaking cell conglomerates by multiple pipetting. The cells were transferred to a sterile centrifuge tube and centrifuged at 1200 rpm for 10 minutes. The supernatant was drained and the cells were transferred to complete growth medium. Then the cells were counted in Gorjaev's chamber and used in the experiments.

Cell cultures that have passed at least 20 and not more than 30 passages can be used to determine activity and toxicity.

Preparation of Vesicular Stomatitis Virus.

For the experiment, freeze-dried vesicular stomatitis virus (VSV), packaged in glass ampoules sealed under sterile conditions, was used.

The virus was grown on the L-929 cell line. To do this, a pre-titrated dose of the virus was added to the vial with a formed monolayer of cells in the complete culture medium (the infectious titer of VSV was the maximum dilution of the virus, which caused the complete destruction of the monolayer of cells during 1 day at 37° C.). The content of the vial was cultured for 1 day at 37° C., after which the culture medium was drained into sterile 50 ml tubes and centrifuged at 2000 rpm. Further, aliquots 1 ml of the supernatant obtained, which contained the vesicular stomatitis virus were dispensed into ampoules under sterile conditions and lyophilized.

The determination of the infectious titer of the virus.

The prepared cells of Л-68 line suspended in complete culture medium 1 at a concentration of $5 \times 10^4$ cells/well in a volume of 0.2 ml were added to the 96-well plate ("Costar" type). After this, the plate was incubated for 1 day at 37 C in a $CO_2$ incubator with atmosphere containing 5% $CO_2$. During this time, the cells covered wells, forming a continuous monolayer. After 1 day, the culture medium was decanted under sterile conditions, and previously prepared two-fold dilutions of the virus were added into the wells of the plate in four duplicates. The VSV virus was added in a complete culture medium in a volume of 0.2 ml. The plate was then incubated under the conditions described above. At the end of the incubation (after 1 day), the culture medium was decanted and 0.05 ml of 0.2% solution of crystalline violet in 20% methanol was added to the wells. After 10 minutes, the dye was removed, the plate was washed under a stream of water and dried. Further, 0.1 ml of the lysis buffer was added to the plate for eluting the dye into the solution. The intensity of staining was recorded on the microplate reader at 595 nm.

The maximum dilution of the virus, which causes the complete destruction of the monolayer of cells in the wells within 1 day under these conditions, is taken as the infectious titer of the virus. The optical density of the solution in these wells will be minimal and close to the background value.

Determination of Activity.

In a complete growth medium, double dilutions (above and below the expected titer) of standard activity sample were prepared (42-28-119-96P; SISC after L. A. Tarasevich), the activity of which was expressed in international units IU. Dilution of the standard was carried out in a 96-well plate ("Costar" type) in a volume of 0.1 ml, with at least 4 wells used for each dilution. One row of the plate was left to control the culture medium (4 wells) and to control the dose of the VSV virus (4 wells). 0.1 ml was added to these wells. After dilution of the standard, the prepared cells of Л-68 line suspended in complete culture medium 1 at a concentration of $5 \cdot 10^4$ cells/well in a volume of 0.1 ml were added to the plate. After this, the studied fractions were added to the part of the rows with diluted standard at certain time intervals:

1—glutathione disulfide S-oxide (compound obtained in Example 1);

2—glutathione disulphide (compound obtained in Example 2);

3—composition of glutathione disulfide S-oxide with glutathione disulphide (composition obtained in Example 5);

4—composition of glutathione disulfide S-oxide with disulfide glutathione and metal, platinum compound Pt-S cisplatin (composition obtained in Example 6)

at concentrations of 0.0015 μmol/ml, 0.015 μmol/ml and 0.15 μmol/ml. Next, each plate was incubated for 1 day at 37° C. in a $CO_2$ incubator with atmosphere containing 5% $CO_2$. During this time, the cells cover wells, forming continuous monolayer. After 1 day, the full growth culture medium was decanted in sterile conditions and the VSV virus with pre-determined infectious titer was added to the wells of each plate. The VSV virus was added in a complete culture medium in a volume of 0.2 ml. 0.2 ml of the same medium without the VSV virus was added into the wells as medium control. After this, each plate was incubated under the conditions described above. At the end of the incubation (after 1 day), the culture medium was decanted and 0.05 ml of a 0.2% solution of crystal violet in 20% methanol was added to the wells. After 10 minutes, the dye was removed, the dish was washed under a stream of water and dried. In the medium control wells, the colored monolayer should be free of signs of destruction. Further, 0.1 ml of the lysis buffer was added to the plate for eluting the dye into the solution. The intensity of staining was recorded on the microplate reader at 595 nm.

The value inverse of the dilution of the preparation, which completely protect cell culture from the cytopathic effect of the virus in 50% of the wells is taken as the interferon titer.

Experiment Results.

It was experimentally established that the preincubation of cells with each test compound had no effect on the antiviral activity of interferon.

The results of the experiments where each composition was added after interferon, point at the ability of virtually all test substances to increase the interferon efficacy if the composition was added not earlier than thirty minutes after cells exposure to interferon.

The test substances increased the efficacy in varying degrees with the interferon titers $6.4 \times 10^{-5}$ to $1.28 \times 10^{-6}$, which was exhibited as greater increase in optical density in the experiment, where the interferon acted together with one or another substance versus experiment where only interferon acted.

To determine more reliable value of the increase in the efficacy of interferon with one or another composition, an experiment was performed to obtain a larger number of experimental data on the dilution of interferon, where its activity was noted (Table 7).

TABLE 7

| | | | Interferon α standard + substance according to Example 1 | Interferon α standard + substance according to Example 2 | Interferon α standard + substance according to Example 5 | Interferon α standard + substance according to Example 6 | |
|---|---|---|---|---|---|---|---|
| Dilution of interferon α | Medium control | Interferon α standard | | | | | Number of observations |
| $0.64 \times 10^{-6}$ | 2.703 ± 0.089* | 1.59 ± 0.131* | 1.73 ± 0.076* | 1.79 ± 0.079* | 1.91 ± 0.096* | 2.57 ± 0.098* | n = 21 |
| $1.28 \times 10^{-6}$ | 2.728 ± 0.172** | 0.905 ± 0.088** | 1.03 ± 0.097** | 1.01 ± 0.137** | 1.72 ± 0.133** | 2.34 ± 0.118** | n = 19 |

*$P < 0.1$
**$P < 0.05$

The results obtained indicate that all test compositions increase the antiviral activity of interferon α in a certain range of its concentrations if they are added after it. A similar nature of the effect of the composition is due to absence or relatively insufficient amount of oxidizing agent in the culture medium when it is pre-administered or co-administered with interferon. The complex composition of the culture medium leads to the relative quick disappearing of the small amounts of the active principle from the culture medium toward the intracellular space. The action of interferon on tropic cells is accompanied by the production of oxidizing agents, however, the time of their production in sufficient quantity exceeds the time, which the metal coordination compound spends in the culture medium. Preliminary adding of interferon and its effect on tropic cells promotes the production of oxidizing agent by these cells, which is subsequently used in catalytic action on sulfhydryl groups of various receptors, including interferon receptors, which eventually contributes, among other, to increase in the number of cells interacting with interferon, and this in turn determines the enhancement of its antiviral effect.

Thus, all test substances are capable to increase the efficacy of the action of interferon α, but metal coordination compound in the formulation of the composition significantly potentiates its activity, increasing the number of cells capable of receptor-mediated interaction with interferon α. Therein, it should be noted that the potentiation of the antiviral effect of interferon α with the substances obtained according to Examples 1 and 2 practically coincides and is 9-10% at different dilutions. The combined action of the substances according to Example 1 and 2 in the form of the composition according to Example 5 makes it possible to obtain additional enhancement of the antiviral effect of interferon α at lower dilutions (up to 18%) and almost double amplification at large dilutions of interferon α, i.e. at lower doses of interferon α. A similar pattern was found when using the composition according to Example 6: the antiviral effect of interferon α was more pronounced, in particular increased by 50% at low dilutions and 2.5 times at deeper ones. The antiviral effect of interferon α in therapeutic doses is associated with the development of dose-dependent side effects and toxic effects in 72% of patients receiving formulations of interferon α. Flu-like syndrome, symptoms of gastrointestinal and psychogenic disorders, signs of myelosuppression, disorders of the functions of the thyroid and parathyroid glands, formation of pool of autoantibodies to the endogenous interferon α of the patient are most often reported among the negative manifestations of the therapy administered. The possibility of use interferon α at lower therapeutic doses in conjunction with the composition according to Example 5 or 6 allows to significantly reduce variety of side effects and toxic dose-dependent reactions to interferon α.

The invention claimed is:

1. A pharmaceutical composition for treating dose-related toxicity and enhancing the therapeutic activity of a pharmacologically active compound in the treatment of infectious and non-infectious diseases, comprising glutathione disulfide or pharmaceutically acceptable organic or inorganic salt thereof and glutathione disulfide S-oxide of the following structure:

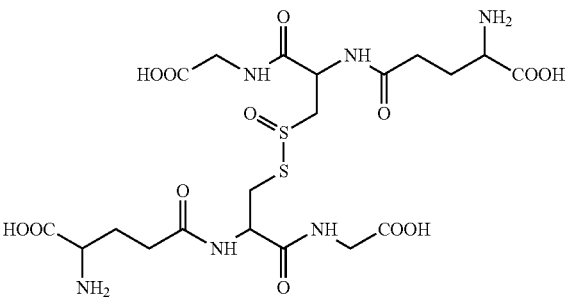 [SMILES: NC(CCC(=O)NC(CSS(=O)CC(NC(=O)CCC(N)C(=O)O)C(=O)NCC(=O)O)C(=O)NCC(=O)O)C(=O)O]

or pharmaceutically acceptable organic or inorganic salt thereof,
wherein said composition further comprises a d-metal (Me) selected from the platinum group, and
wherein the amount of d-metal in the composition ranges from $1 \times 10^{-10}$ moles to $1 \times 10^{-3}$ moles per 1 kg of the composition.

2. The pharmaceutical composition of claim 1, wherein the amount of glutathione disulfide S-oxide is 0.01-10% by weight of the total composition.

3. The pharmaceutical composition of claim 1, wherein the metal is platinum.

4. The pharmaceutical composition of claim 1, wherein the amount of d-metal in the composition is $1 \times 10^{-5}$ moles per 1 kg of the composition.

5. A pharmacological combination for treating dose-dependent toxicity and enhancing the therapeutic activity of a pharmacologically active compound in the treatment of infectious and non-infectious diseases, comprising the composition of claim 1 and pharmacologically active compound selected from the group of anticoagulant, factor Xa inhibitor, antimicrobial or antiviral agent, calcium channel inhibitor.

6. The pharmacological combination of claim 5, wherein non-infectious disease is thromboses, where the pharmacologically active compound is anticoagulant, factor Xa inhibitor amidine hydrochloride.

7. The pharmacological combination of claim 5, wherein said infectious disease is caused by Gram-negative and Gram-positive bacteria, selected from the group consisting of *Escherichia coli, Pseudomonas aeruginosa, Acineto-*

*bacter baumannii, Listeria monocytogenes* EGD, *Staphylococcus aureus*, MRSA—methicillin-resistant *Staphylococcus aureus*, and wherein the pharmacologically active compound is antimicrobial agent moxifloxacin.

8. The pharmacological combination of claim 5, wherein the infectious disease is a viral disease, where the pharmacologically active compound is antiviral agent.

9. The pharmacological combination of claim 8, wherein the viral disease is rabies, wherein the pharmacologically active compound is antigenic material of anti-rabies vaccine.

10. A medicament for treating dose-related toxicity and enhancing the therapeutic activity of a pharmacologically active compound in the treatment of infectious and non-infectious diseases, comprising at least one pharmaceutical composition according to claim 1 in a therapeutically effective amount together with pharmaceutically acceptable excipients.

11. A medicament for treating dose-related toxicity and enhancing the therapeutic activity of a pharmacologically active compound in the treatment of infectious and non-infectious diseases, comprising at least one pharmacological combination according to claim 5 in a therapeutically effective amount together with pharmaceutically acceptable excipients.

12. The medicament for treating dose-related toxicity and enhancing the therapeutic activity of a pharmacologically active compound in the treatment of infectious and non-infectious diseases, according to claim 10, wherein said medicament can be manufactured for external, inhalational, enteral or parenteral administration.

13. A method of treating a second phase of xenobiotic detoxification by administering the pharmaceutical composition of claim 1.

14. A method of treating a viral diseases associated with interferon alpha activity by administering the pharmaceutical composition of claim 1.

* * * * *